United States Patent
Hofko et al.

(10) Patent No.: US 10,527,547 B2
(45) Date of Patent: Jan. 7, 2020

(54) METHOD AND DEVICE FOR DETERMINING A MATERIAL PROPERTY OF A BITUMEN MATERIAL

(71) Applicant: TECHNISCHE UNIVERSITAET WIEN, Vienna (AT)

(72) Inventors: Bernhard Hofko, Vienna (AT); Markus Hospodka, Moedling (AT); Josef Fuessl, Oxford (GB); Lukas Eberhardsteiner, Vienna (AT); Hinrich Grothe, Bisamberg (AT); Florian Handle, Vienna (AT); Daniel Grossegger, Saalfelden (AT); Ronald Blab, Langenzersdorf (AT)

(73) Assignee: TECHNISCHE UNIVERSITÄT WIEN, Vienna (AT)

(*) Notice: Subject to any disclaimer, the term of this patent is extended or adjusted under 35 U.S.C. 154(b) by 37 days.

(21) Appl. No.: 15/739,123

(22) PCT Filed: Jun. 22, 2016

(86) PCT No.: PCT/AT2016/050219
§ 371 (c)(1),
(2) Date: Dec. 21, 2017

(87) PCT Pub. No.: WO2016/205847
PCT Pub. Date: Dec. 29, 2016

(65) Prior Publication Data
US 2018/0188174 A1 Jul. 5, 2018

(30) Foreign Application Priority Data
Jun. 22, 2015 (AT) .................................. 50522/2015

(51) Int. Cl.
*G01N 21/64* (2006.01)
*G01N 33/42* (2006.01)

(52) U.S. Cl.
CPC ............. *G01N 21/64* (2013.01); *G01N 33/42* (2013.01); *G01N 2021/6419* (2013.01); *G01N 2201/061* (2013.01); *G01N 2201/12* (2013.01)

(58) Field of Classification Search
CPC .... G01N 21/64; G01N 33/42; G01N 2201/12; G01N 2201/061; G01N 2021/6419
(Continued)

(56) References Cited

U.S. PATENT DOCUMENTS

| 4,957,366 A | 9/1990 | Koshi et al. |
| 4,959,549 A * | 9/1990 | Haub ..................... G01N 21/64 250/358.1 |

(Continued)

FOREIGN PATENT DOCUMENTS

| DE | 68912156 T2 | 4/1994 |
| DE | 19523806 A1 | 1/1997 |

(Continued)

OTHER PUBLICATIONS

Handle, F. et al., "Confocal Laser Scanning Microscopy-Observation of the Microstructure of Bitumen and Asphalt Concrete," Proceedings of the 5th Eurasphalt & Eurobitume Congress, Jun. 13, 2012, Istanbul, Turkey, 8 pages.

(Continued)

*Primary Examiner* — David P Porta
*Assistant Examiner* — Meenakshi S Sahu
(74) *Attorney, Agent, or Firm* — McCoy Russell LLP (57) ABSTRACT

The invention relates to a method and to a device for determining a material property, in particular the aging state or the aging resistance, of a bitumen material, comprising the steps: applying a substantially monochromatic first excitation radiation of a first excitation wavelength to the bitumen material; measuring the intensity of a first fluorescence radiation, excited by the first excitation radiation, at a (Continued)

measurement wavelength; applying a substantially monochromatic second excitation radiation of a first excitation wavelength to the bitumen material; measuring the intensity of a second fluorescence radiation, excited by the second excitation radiation, at the measurement wavelength; determining a first key figure for the material property of the bitumen material from the ratio between the intensity of the second fluorescence radiation to the intensity of the first fluorescence radiation.

16 Claims, 3 Drawing Sheets

(58) Field of Classification Search
  USPC .................................................. 250/459.1
  See application file for complete search history.

(56) References Cited

U.S. PATENT DOCUMENTS

| | | |
|---|---|---|
| 5,241,184 A | 8/1993 | Menzel |
| 5,614,670 A | 3/1997 | Nazarian et al. |
| 5,780,850 A | 7/1998 | DeLaune et al. |
| 2012/0135431 A1 | 5/2012 | Yokoyama |
| 2012/0326055 A1 | 12/2012 | Wilson et al. |

FOREIGN PATENT DOCUMENTS

| | | |
|---|---|---|
| DE | 102007055045 A1 | 11/2008 |
| JP | 2005337885 A | 12/2005 |
| KR | 20070081842 A | 8/2007 |

OTHER PUBLICATIONS

ISA European Patent Office, International Search Report and Written Opinion Issued in Application No. PCT/AT2016/050219, dated Oct. 19, 2016, WIPO, 6 pages.

The International Bureau of WIPO, International Preliminary Report on Patentability Issued in Application No. PCT/AT2016/050219, dated Jan. 4, 2018, WIPO, 8 pages.

* cited by examiner

Fig. 1

Fig. 2

METHOD AND DEVICE FOR DETERMINING A MATERIAL PROPERTY OF A BITUMEN MATERIAL

CROSS-REFERENCE TO RELATED APPLICATIONS

The present application is a U.S. National Phase of International Patent Application Serial No. PCT/AT2016/050219 entitled "METHOD AND DEVICE FOR DETERMINING A MATERIAL PROPERTY OF A BITUMEN MATERIAL," filed on Jun. 22, 2016. International Patent Application Serial No. PCT/AT2016/050219 claims priority to Austrian Patent Application No. A 50522/2015, filed on Jun. 22, 2015. The entire contents of each of the above-cited applications are hereby incorporated by reference for all purposes.

TECHNICAL FIELD

The invention relates to a method and a device for determining a material property of a bitumen material, which property is particularly associated with the ageing state or ageing resistance thereof.

BACKGROUND AND SUMMARY

Bitumen and bituminous materials are important raw materials in construction, industry and production. Particularly in the construction industry, the requirements imposed on material and product are increasing constantly, necessitating improved quality control and analysis of the materials. The more stringent requirements relate particularly to the material's resistance to ageing, which previously could only be determined approximately with time-consuming tests. In the past a basic, rapid test of ageing resistance that enables a quality check to be carried out in various stages of the work process has been missed most of all. In particular, it would be desirable to capture material properties of the bitumen in the production, storage and processing processes, without requiring substantial amounts of time therefor.

This relates to the recycling of road construction bitumen, for example. This is understood to include the reuse of bound bituminous building material, which arises in large quantities particularly in road construction. In principle, most reclaimed asphalts can be reused to produce new asphalt mixture. However, the rate of reuse of reclaimed asphalt remains low. This is due in particular to the fact that there is no reliable quality control for the recycled material.

At the moment, the signs of ageing in recycling asphalt are reduced by adding very soft, fresh binding agent. However, the disadvantage of this method is that it is not efficient. Therefore, it is imperative to include the ageing mechanism of bitumen on the chemicophysical level in order to be able to predict the reusability of reclaimed asphalt reliably.

Various approaches therefor have been presented in the related art.

With regard to ageing mechanisms in long-term ageing, use is often made of a refinement of a micelle model for bitumen. The micelle model states that bitumen consists of a continuous oily phase (maltene phase), in which asphaltene micelles of agglomerated asphaltene molecules are dispersed (emulsion). In order for the highly polar asphaltene micelles to be able to disperse successfully in the low polarity maltene phase, a shell is needed around the micelles to create a polarity gradient (emulsifier). This shell is constructed from aromatics and resins. When oxidising agents attack, they first penetrate the maltene phase, but this is very weakly reactive. Vigorous oxidation only begins at the shell of the particles, which in turn results in an increase of polarity at the boundary surface between the shell and the maltene phase. This reduces the quality of the dispersion, a kind of predetermined breaking point is created at the boundary surface, giving rise to increased hardness and brittleness of the material and thus facilitating the formation of brittle fractures. This may explain how the advance of ageing leads to increased brittleness. Tests conducted by the Applicant have shown that the mechanical behaviour of neither the maltene phase nor the asphaltenes changes substantially as a result of ageing. The increasing stiffness of bitumen which accompanies the advance of ageing may be explained by the increase in the asphaltene concentration relative to the concentration of smaller, less polar aromatics, and described by modelling.

In order to investigate these processes, particular use was made of the techniques of fluorescence spectroscopy and fluorescence microscopy, which are known per se in the related art (see Handle, Florian, et al. "Understanding the microstructure of bitumen: a CLSM and fluorescence approach to model bitumen ageing behavior." *Proceedings to* 12*th ISAP International Conference on Asphalt Pavements*, Raleigh, USA 2014; Handle et al. "The bitumen microstructure: a fluorescent approach", *Materials and Structures*, December 2014; Bearsley et al. "Direct observation of the asphaltene structure in paving-grade bitumen using confocal laser-scanning microscopy, *Journal of Microscopy*, Vol. 215, 2004). These investigations helped to gain a better understanding of the ageing of bitumen.

A wide variety of apparatuses was also suggested in the related art for measuring fluorescence (see for example CA 2 833 299, US 2005/0253088 A1, U.S. Pat. No. 4,330,207, WO 2010/048584, U.S. Pat. No. 7,633,071 B2, US 2014/0135431 A1).

Until now, however, no satisfactory solution has been found as to how the theoretical knowledge regarding the ageing process of bitumen gained with the aid of fluorescence spectroscopy might be translated into a practically viable method for analysing the suitability of reclaimed asphalt for reuse.

In JP 2005-337885 A, a novel method is described in an unrelated field for determining the degree of wear of a cable with the aid of fluorescence spectroscopy. The method is designed to enable the cable to be replaced in a timely manner when a certain degree of wear is reached. The cable material is excited with a broadband excitation radiation, and then the shift of the fluorescence signal is measured. However, this method is not intended for use in characterising bitumen, nor would it be suitable therefor.

In view of the above, the object of the invention consists in alleviating or eliminating the disadvantages of the related art. The stated objective of the invention is therefore particularly to provide a method with which the material properties of a bitumen material can be determined quickly and simply. In addition, a device of simple design is to be provided for determining the material properties of the bitumen material.

This object is solved with a method for determining a property of a bitumen material, in particular an ageing state or an ageing resistance of the bitumen material, comprising the steps: applying a substantially monochromatic first excitation radiation having a first excitation wavelength to the bitumen material; measuring an intensity of a first fluorescence radiation excited by the first excitation radiation in a measurement wavelength range; applying a substantially monochromatic second excitation radiation having a second excitation wavelength to the bitumen material; measuring an intensity of a second fluorescence radiation excited by the second excitation radiation in the measurement wavelength range; and determining a first characteristic number for the material property of the bitumen material from a ratio between the intensity of the second fluorescence radiation and the intensity of the first fluorescence radiation; and a device for determining a material property, in particular the ageing state or the ageing resistance of a bitumen material, having a first radiation device for applying a substantially monochromatic first excitation radiation having a first excitation wavelength to the bitumen material; a second radiation device for applying a substantially monochromatic second excitation radiation having a second excitation wavelength to the bitumen material; a measuring device for measuring the intensity of a first fluorescence radiation excited by the first excitation radiation in a predetermined measurement wavelength range and for measuring the intensity of a second fluorescence radiation excited by the second excitation radiation in the predetermined measurement wavelength range; and a processing unit with a first ratio forming function for determining a first characteristic number for the material property of the bitumen material from the ratio between the intensity of the second fluorescence radiation and the intensity of the first fluorescence radiation. Embodiments are described in the dependent claims. An alternative solution for the same object is solved by a method for determining a material property of a bitumen material, comprising the steps: applying a substantially monochromatic excitation light to the bitumen material; measuring an intensity of a first fluorescence signal excited by the excitation light at a first emission wavelength; measuring an intensity of a second fluorescence signal excited by the excitation light at a second emission wavelength; determining a first characteristic number for the material property of the bitumen material from a ratio between the intensity of the second fluorescence signal at the second emission wavelength and the intensity of the first fluorescence signal at the first emission wavelength.

The method according to the invention thus comprises at least the following steps:
a. Applying a substantially monochromatic first excitation radiation having a first excitation wavelength to the bitumen material;
b. Measuring the intensity of a first fluorescence radiation excited by the first excitation radiation in a measurement wavelength range;
c. Applying a substantially monochromatic second excitation radiation having a second excitation wavelength to the bitumen material;
d. Measuring the intensity of a second fluorescence radiation excited by the second excitation radiation in the measurement wavelength range;
e. Determining a first characteristic number for the material property of the bitumen material from the ratio between the intensity of the second fluorescence radiation and the intensity of the first fluorescence radiation.

According to the invention, the bitumen material, particularly reclaimed or recycling asphalt, is exposed to a first excitation radiation having a first excitation wavelength, with which particularly the fluorescing centres of the bitumen are excited to a first emission of fluorescence radiation, the intensity of which is captured in a predetermined measurement wavelength range. The first fluorescence radiation is preferably captured in a substantially monochromatic measurement wavelength range, i.e. a single measurement wavelength is used. Alternatively, a measurement wavelength range may be used which is small compared to the wavelength range in which the first fluorescence radiation occurs. The bitumen is also irradiated with a second excitation radiation having a second excitation wavelength which is different from the first excitation wavelength. The excitations of the bitumen material are preferably separated by a time interval in order to guarantee the resolution between the measurement signals of the first and second fluorescence radiations and fluorescence emissions. The intensity of the second fluorescence radiation is captured in the same measurement wavelength range as the first fluorescence radiation. As described previously, on the one hand the measurement wavelength range may be substantially monochromatic. On the other hand, the intensity of the second fluorescence radiation may be captured in a range of measurement wavelengths that is narrow compared to the overall wavelength range of the second fluorescence radiation. Finally, a characteristic number (classification value) is determined for the material property, particularly for the ageing state or ageing resistance of the bitumen from the ratio between the intensity of the second fluorescence radiation and the intensity of the first fluorescence radiation. In extensive research, it was found in particular that the ageing processes in the bitumen material affect its fluorescence spectrum. The method according to the invention exploits this finding by measuring the intensity of the fluorescence radiation at two different, discrete excitation wavelengths, wherein the ratio between the intensities of the fluorescence signals is included as a characteristic number (indicator value) particularly for the ageing state of the bitumen material. The second excitation wavelength is preferably larger than the first excitation wavelength. It was demonstrated that it is not necessary to record a complete excitation spectrum (described as an "excitation scan") in order to determine the ageing of the bitumen material. Instead, it was revealed to be sufficient if the intensities of the fluorescence radiation were captured for discrete (i.e. substantially monochromatic) excitation radiations. In this context, the intensity of the first fluorescence radiation is used as the reference value, to which the intensity of the second fluorescence radiation is compared. The ratio between the intensity values of the fluorescence radiation on the different excitation wavelengths may be a reliable indicator as to whether the ageing processes have had a detrimental effect on the material properties of the bitumen material under examination. Moreover, the first characteristic number may be used in a preliminary test as to whether insufficient ageing resistance in the bitumen material due to poor raw material quality, storage conditions, processing etc. threatens to have a significant negative impact on the material properties in the near future. Accordingly, in a preferred application the first characteristic number may be used as a measure of the ageing resistance of the bitumen material, which may be in particular a reclaimed or recycling asphalt. In experimental analyses, it was shown in particular that the ageing of the bitumen material causes the intensity of the second fluorescence radiation to fall in proportion to the first fluorescence radiation. Thus, the characteristic number determined enables an estimation to be made of the ageing state or ageing resistance of the bitumen material under examination. The higher the first characteristic number, the greater the ageing resistance of the bitumen material. Consequently, it can be decided on that basis of the first characteristic number whether the bitumen material should be provided for initial use, reuse or recycling. By using individual, substantially monochromatic excitation signals it is possible to keep the construction effort for implementing the method low. Advantageously, it is not necessary to scan the excitation spectrum over a wide range of excitation wavelengths. According to the invention, the ageing state of the bitumen materials can be analysed with a very small number of fluorescence measurements. As a result, the time required for performing the method can also be reduced substantially, thus in particular enabling a real-time application of the method, with a hand-held device for example. In order to apply the substantially monochromatic excitation radiation to the bitumen sample, as one alternative radiation sources may be used that emit substantially monochromatic radiation, i.e. radiation with a very small bandwidth. Light emitting diodes or lasers lend themselves particularly well to this. Alternatively, radiation sources such as gas lamps may be used; these emit a broadband excitation radiation, from which the desired, substantially monochromatic excitation radiation is obtained with the aid of a filter or monochromator.

The method according to the invention is particularly suitable for implementation on a portable hand-held device on which only the wavelengths that are also essential for an assessment of the ageing state are excited. Thus, a method may be provided for the first time with which the ageing resistance of the bitumen used may be evaluated easily, quickly and inexpensively, and which may be performed flexibly, in the laboratory, on the construction site, and even in the constructed state.

If the first characteristic number is compared with a first reference value for the material property of the bitumen material, a decision may be reached particularly easily as to whether the bitumen material under examination can be added to a first use or reuse application, or if the ageing resistance of the bitumen material is already so degraded that first use or reuse of the bitumen material would not be expedient since significant damage due to material ageing is to be expected in the near future. Accordingly, deficient quality of the bitumen material in terms of the ageing state and/or ageing resistance may be established if the first characteristic number is lower than the first reference value. The reference value may be derived on the one hand from theoretical considerations or empirical values from earlier analyses of bitumen materials with various degrees of ageing. The reference value is preferably stored in a database. When the method is performed, the reference value is retrieved from the database to enable comparison with the first characteristic number, which was determined from the measurement values of the fluorescence radiation on different excitation wavelengths.

Research revealed that it was not possible to establish ageing reliably on the basis of the first characteristic number alone for all bitumen samples. It was found that in some bitumen samples the first characteristic number is unremarkable, yet the material properties are already significantly impaired due to complex processes such as ageing in previous use or thermal damage during storage etc. In order to make this class of bitumen materials accessible to the method for establishing ageing, a preferred variant of the method comprises performing following additional steps:
a. Applying a substantially monochromatic third excitation radiation having a third wavelength to the bitumen material;
b. Measuring the intensity of a third fluorescence radiation excited by the third excitation radiation in the measurement wavelength range;
c. Determining a second characteristic number for the material property of the bitumen from the ratio between the intensity of the third fluorescence radiation and the intensity of the first fluorescence radiation.

In this variant, the fluorescence emission of the bitumen material due to excitation with the third excitation radiation having the third excitation wavelength is measured, wherein the third excitation wavelength is different from both the first and the second excitation wavelengths. The intensity of the third fluorescence radiation, which may be measured following a time interval after the first and second fluorescence radiations, is then placed in proportion with the intensity of the first fluorescence radiation to obtain a second characteristic number particularly for the ageing state of the bitumen material.

In this way, ageing resistant bitumen samples may be reliably differentiated from those bitumen samples whose first characteristic number is higher than the first reference value but which have nevertheless undergone profound ageing processes. In this context, it is of no importance whether the causes of the ageing processes, reside in long-term changes during the service period of a recycling material or in material damage due to poor storage or processing.

In order to be able to establish the quality of the bitumen material under examination in simple manner, it is advantageous if the second characteristic number is compared with a second reference value. Thus with this step the use of the bitumen material in a first use or reuse application may be made dependent on whether the first characteristic number is greater than the first reference value and the second characteristic number is greater than the second reference value.

Extensive experiments on the fluorescence of bitumen have revealed that certain excitation wavelength are particularly favourable for determining the material property under examination, particularly the ageing state of the bitumen material. The first excitation wavelength of the first excitation radiation is preferably selected from a wavelength range between 260 and 280 nanometers. When the bitumen is excited in said wavelength range, the global maximum for fluorescence of the bitumen is obtained, and the intensity thereof can supply supplementary information about the ageing state. However, the intensity of the observed emission may also be heavily influenced by the measurement and sample setup, particularly with regard to focus and distances. These influences may present difficulties particularly in the case of rough sample surfaces. On the other hand, the ratio of the intensities is substantially independent of the measurement and sample geometry, provided the residual intensity is sufficient. Experiments have shown in particular that the ratio between the intensities of the different fluorescence maxima allows a reliable conclusion to be drawn about the material property under investigation. Accordingly, the first excitation wavelength from the range of the global fluorescence maximum lends itself particularly well to use as a reference value for loss of fluorescence intensity due to ageing, which may be established with larger wavelengths of the excitation radiation.

According to a particularly preferred variation, it is provided that the second excitation wavelength of the second excitation radiation is selected from a wavelength range between 350 and 380 nanometers. It was demonstrated in fluorescence analyses that the intensity of the fluorescence radiation exhibits a local maximum or spectral ridge between 350 and 380 nanometers. Accordingly, the second excitation wavelength is selected from a local extreme point of the fluorescence, at which the derivative function of the fluorescence signal assumes the value of substantially zero.

One advantage of this variant is that the ageing-induced deviation of the intensity of the fluorescence radiation is particularly large in the range of the local maximum. At the same time, it enables the measurement accuracy to be increased because the change in the fluorescence signal is small in the range of the local maximum.

It is also favourable if the third excitation wavelength of the third excitation radiation is selected from a wavelength range between 470 and 500 nanometers. The fluorescence spectrum of the bitumen material exhibits a further local maximum in this wavelength range, so for reasons explained earlier it is particularly advantageous to determine the fluorescence with an excitation in this wavelength range.

In some cases, it may be beneficial if the intensity of a fourth fluorescence radiation is captured, this being excited with a substantially monochromatic fourth excitation radiation having a fourth excitation wavelength between 440 and 460 nm. A further spectral ridge of the fluorescence spectrum occurs in this range, and may be used for analysing the material property. However, this local maximum is relatively weakly defined consequently more susceptible to error than the local maxima for fluorescence radiation described previously.

Extensive experiments have revealed that the ranges identified for the first and second excitation wavelengths are characteristic for certain fractions of the bitumens, called aromatics and resins, which have a significant effect on the structural and mechanical properties of bitumen. By analysis of the fluorescence upon excitation of the bitumen material with the preferred values for the first and second excitation wavelengths, it is possible to determine the frequency, stability and chemical resistance to oxidation of the aromatics and resins. For this purpose, preferably the first and second characteristic numbers are calculated for use in estimating the ageing resistance of the bitumen material under investigation.

According to a preferred embodiment, the measurement wavelength range is substantially monochromatic with a measurement wavelength between 390 and 650 nanometers, particularly substantially 525 nanometers. This variant advantageously yields a maximum signal.

The device according to the invention for determining a material property, particularly the ageing state and/or ageing resistance of a bitumen material includes at least the following components:
a. a first radiation device for applying a substantially monochromatic first excitation radiation of a first excitation wavelength to the bitumen material;
b. a second radiation device for applying a substantially monochromatic second excitation radiation of a second excitation wavelength to the bitumen material;
c. a measuring device for measuring the intensity of a first fluorescence radiation in a predetermined measurement wavelength range excited by the first excitation radiation, and for measuring the intensity of a second fluorescence radiation in the predetermined measurement wavelength range excited by the second excitation radiation;
d. a processing unit with a first ratio forming function for determining a first characteristic number for the material property of the bitumen material from the ratio between the intensity of the second fluorescence radiation and the intensity of the first fluorescence radiation.

The device provides the same advantages as the method described in the preceding text, so reference is simply made to the earlier notes. The essential characteristic for the invention is that particularly simple radiation devices may be used, since the first characteristic number for material property, particularly the ageing of the bitumen material is determined from just two fluorescence signals which are scanned on two discrete excitation wavelengths. On the other hand, it is in particular not necessary to configure the equipment for radiating, measuring and calculating for the purpose of analysing an excitation spectrum over a wide wavelength range of the excitation wavelength.

In order to identify the bitumen samples that are unsuitable for initial use or reuse, the device for determining the material property of the bitumen material preferably also includes the following components:
a. a third radiation device for applying a substantially monochromatic third excitation radiation of a third excitation wavelength to the bitumen material, wherein the measuring device is configured for measuring the intensity of a third fluorescence radiation excited by the third excitation radiation in the predetermined measurement wavelength range;
b. a second ratio forming function for determining a second characteristic number for the material property of the bitumen material from the ratio between the intensity of the third fluorescence radiation and the intensity of the first fluorescence radiation.

In order to establish the usability of the bitumen material simply, it is advantageous if the processing unit has a first database with a first reference value for the material property of the bitumen material and a first comparison module for comparing the first characteristic number with the first reference value, wherein the processing unit preferably has a second database with a second reference value for the material property of the bitumen material and a second comparison module for comparing the second characteristic number with the second reference value. If the first characteristic number falls below the first reference value, according to a preferred application of the method the bitumen material may be excluded from first use or reuse and recycling. Moreover, the bitumen material will then not be put to any use without further measures if the first characteristic number is higher than the first reference value but the second characteristic number is lower than the second reference value. The used bitumen material only has the required material properties if the first characteristic number is larger than the first reference value and the second characteristic number is larger than the second reference value, so that the selection process may be substantially improved.

According to a particularly preferred variant, the first and second radiation devices differ from each other, wherein the first radiation device is configured to emit the substantially monochromatic first excitation radiation on the first excitation wavelength and the second radiation device is configured to emit the substantially monochromatic excitation radiation on the second excitation wavelength.

To this end, it is advantageous if the first radiation device has a first LED for emitting the first excitation radiation on the first excitation wavelength and/or the second radiation device has a second light emitting diode for emitting the second excitation radiation on the second excitation wavelength and/or the third radiation device has a third light emitting diode for emitting the third excitation radiation on the third excitation wavelength. Instead of the light emitting diodes, diode lasers may be used.

According to a further preferred variant, the first and second radiation devices, optionally the third radiation device as well are formed by one joint radiation device, which is equipped with a radiation source for emitting a broadband excitation radiation. In this variant, a device for selecting the first, second and optionally third excitation wavelengths is provided between the radiation source for the broadband excitation radiation and the bitumen material, and which is formed by a filter or a monochromator for example.

In order to provide the user of the device with information about the material property, particularly the ageing state of the bitumen material, it is favourable if the device also has a display unit for displaying the first and/or second characteristic number and/or the first reference value and/or the second reference value for the material property of the bitumen material. Such display units, such as display screen, as sufficiently well known in the related art and do not need to be described in greater detail for these purposes.

The object underlying the invention is alternatively solved with a method for determining a material property, particularly the ageing state and/or the ageing resistance of a bitumen material having the following steps:

a. Applying a substantially monochromatic excitation light to the bitumen material;
b. Measuring the intensity of a first fluorescence signal excited by the excitation light at a first emission wavelength;
c. Measuring the intensity of a second fluorescence signal excited by the excitation light at a second emission wavelength;
d. Determining a first characteristic number for the material property of the bitumen material from the ratio between the intensity of the second fluorescence signal at the second emission wavelength and the intensity of the first fluorescence signal at the first emission wavelength.

Unlike the embodiment of the invention described previously, in this variant single or discrete intensity values of the emission spectrum (on a first emission wavelength, and a second emission wavelength different from the first) generated by their excitation with a substantially monochromatic excitation light are used to form the first characteristic number, particularly for the ageing state of the bitumen material. Both variants of the invention are associated with the advantage that it is not necessary to scan an entire spectrum, that is to say the excitation spectrum in the first design variant and the emission spectrum in the second design variant of the invention, because the material property, particularly the ageing state or the resistance to ageing of the bitumen material may already be determined reliably from the individual measurement values of the fluorescence.

In order to be able to reliably establish the deterioration of the material properties of the bitumen due to ageing, the method described above may also be supplemented advantageously with the following steps:

a. Measuring the intensity of a third fluorescence signal excited by the excitation light at a third emission wavelength;
b. Determining a second characteristic number for the material property of the bitumen from the ratio between the intensity of the third fluorescence signal at the third emission wavelength and the intensity of the first fluorescence signal at the first emission wavelength.

According to the alternative solution to the stated object of the invention as described above, the device for determining a material property, particularly the ageing state or ageing resistance of a bitumen material includes at least the following components:

a. A radiation unit for applying a substantially monochromatic excitation light to the bitumen material;
b. A measuring unit for measuring the intensity of a first fluorescence signals excited by the excitation light at a first emission wavelength and for measuring the intensity of a second fluorescence signal excited by the excitation light at a second emission wavelength;
c. A calculating unit for determining a first characteristic number for the material property of the bitumen material from the ratio between the intensity of the second fluorescence signal at the second emission wavelength and the intensity of the first fluorescence signal at the first emission wavelength.

BRIEF DESCRIPTION OF FIGURES

In the following text, the invention will be explained further with reference to a preferred embodiment thereof, to which it is not be limited. In the drawing.

DETAILED DESCRIPTION OF FIGURES

Figure 1:
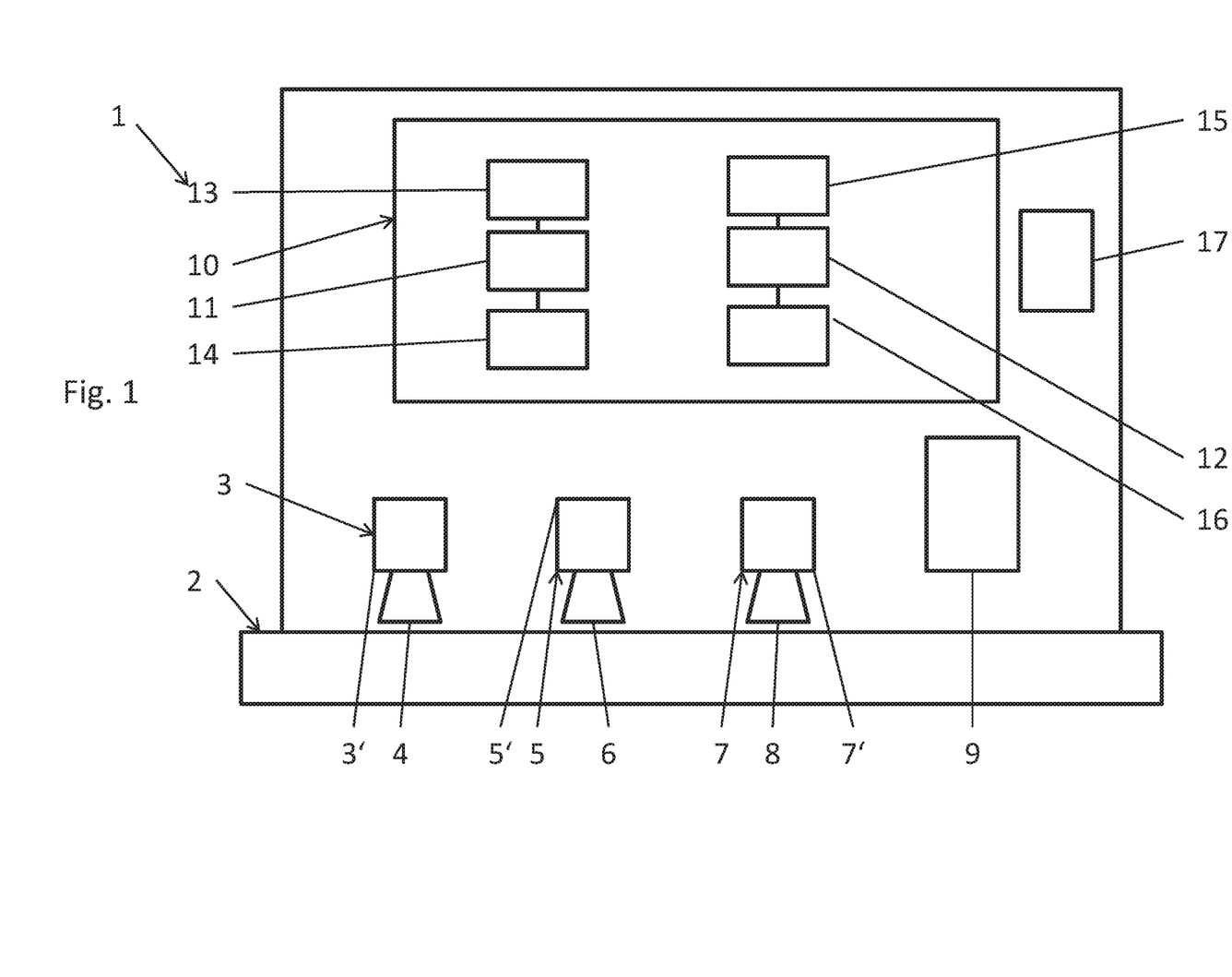
FIG. 1 is a schematic representation of a device for determining the ageing state of a bitumen material.

FIG. 1 is a schematic representation of a device 1 for determining the ageing state of a bitumen material 2, i.e. material that contains the binding agent bitumen. The bitumen material 2 is provided particularly in the form of reclaimed asphalt, of which the ageing resistance is to be investigated with a view to recycling.

Device 1 is equipped with a first radiation device 3 for emitting a substantially monochromatic first excitation radiation 4 of a first excitation wavelength $\lambda 1$. Device 1 is also equipped with a second radiation device 5 for emitting a substantially monochromatic second excitation radiation 6 of a second excitation wavelength $\lambda 2$. Finally, device 1 is equipped with a third radiation device 7 for emitting a substantially monochromatic third excitation radiation 8 of a third excitation wavelength $\lambda 3$. Device 1 is also equipped with a conventional measuring device 9 known per se in the related art, which is configured to measure the intensity I1 of a first fluorescence radiation excited by the first excitation radiation 4 in the bitumen material 2, the intensity I2 of a second fluorescence radiation excited by the second excitation radiation 6, and the intensity I3 of a third fluorescence radiation excited by the third excitation radiation 8. In each case, the fluorescence is measured at the same, predetermined measurement or emission wavelength of 515 nanometers, for example. For this purpose, in the design shown the first radiation device 3, the second radiation device 5 and the third radiation device 7 are activated one after the other, wherein measuring device 9 captures each of the first fluorescence radiation 4, the second fluorescence radiation 6 and the third fluorescence radiation 8 radiated by the bitumen material. As an alternative to activating the first 3, second 5 and third radiation device 7 with a time delay between them, alternating filter sets or screens may be used. In the design shown, a first light emitting diode 3' is provided as the first radiation device 3, a second light emitting diode 5' is provided as the second radiation device 5, and a third light emitting diode 7' is provided as the third radiation device 7.

The individual components of device 1 are known in various embodiments in the related art (see for example CA 2 833 299, US 2005/0253088 A1, U.S. Pat. No. 4,330,207, WO 2010/048584, U.S. Pat. No. 7,633,071 B2), and require no more detailed explanation for these purposes.

As is also shown in FIG. 1, device 1 is further equipped with a processing unit 10 with a first ratio forming function (unit) 11 for determining a first characteristic number K1 for the ageing state of the bitumen material from the ratio between the intensity I2 of the second fluorescence radiation and the intensity I1 of the first fluorescence radiation. Processing unit 10 also includes a second ratio forming function (unit) 12 for determining a second characteristic number K2 for the ageing state of the bitumen material 2 from the ratio between the intensity I3 of the third fluorescence radiation and the intensity I1 of the first fluorescence radiation.

In order to prepare the decision regarding reuse of the bitumen material 2 under examination, processing unit 10 has a first database 13 with a first reference value R1 for the ageing state of the bitumen material 2 and a first comparison module 14 for comparing first characteristic number K1 with first reference value R1. Processing unit 10 also has a second database 15 with a second reference value R2 for the ageing state of the bitumen material and a second comparison module 16 for comparing the second characteristic number with the second reference value. First reference value R1 and second reference value R2 are characteristic for ageing-resistant bitumen materials 2.

As is further shown in FIG. 1, device 1 is also equipped with a display unit 17 for displaying first characteristic number K1 and/or second characteristic number K2 and/or first reference value R1 and/or second reference value R2 for the ageing state of bitumen material 2.

Figure 2:
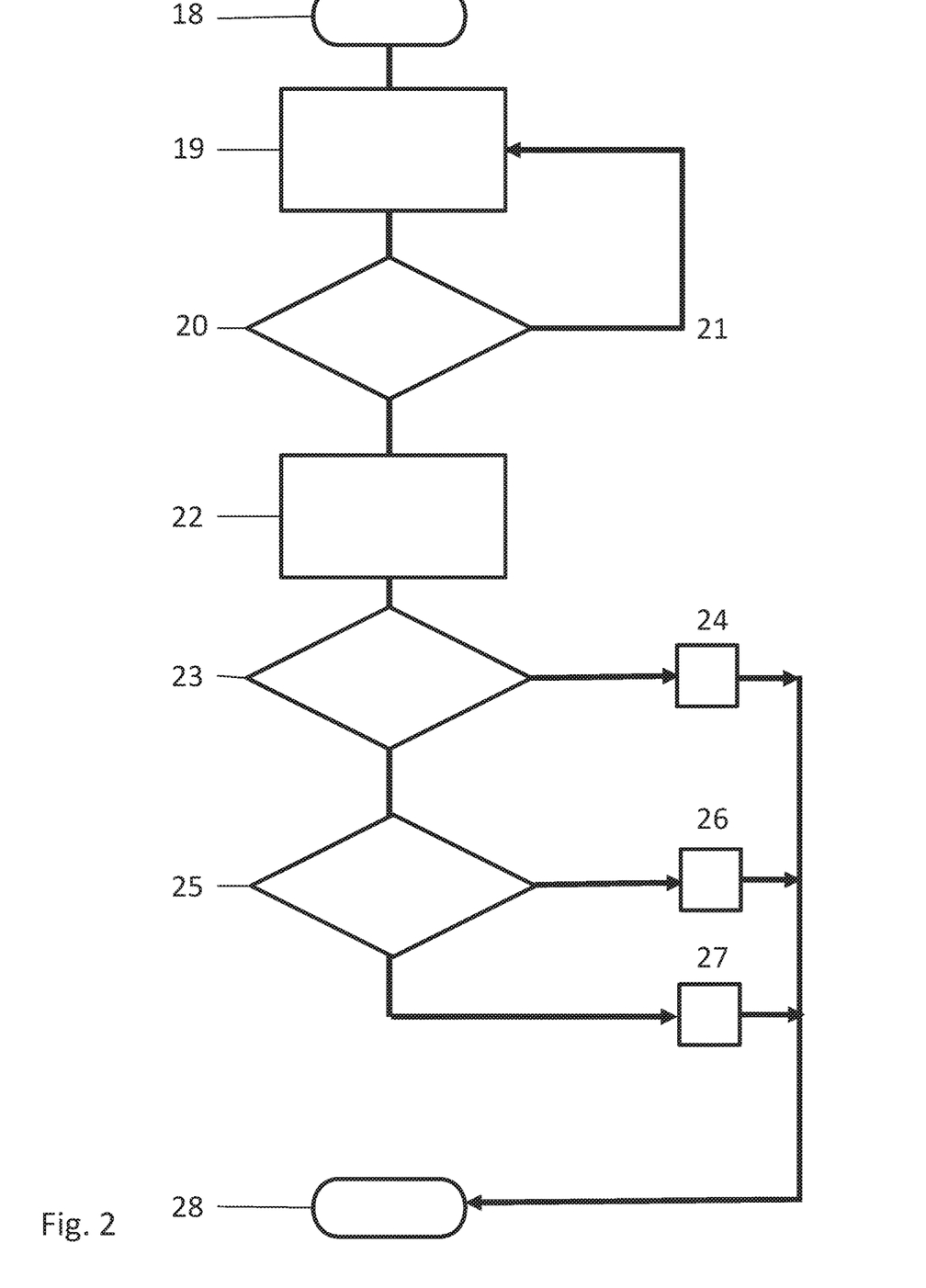
FIG. 2 is a flowchart illustrating a performance variant of the method according to the invention for determining the ageing state of the bitumen material.

The method according to the invention is illustrated in the flowchart of FIG. 2. Following the start 18 of the method, intensity I1 of the first fluorescence radiation, intensity I2 of the second fluorescence radiation and intensity I3 of the third fluorescence radiation are captured (field 19). Then a measurement is taken to determine whether intensity I1 of the first fluorescence radiation is greater than intensity I2 of the second fluorescence radiation, and intensity I3 of the third fluorescence radiation is greater than a threshold value Imin (field 20). If this is not the case, the fluorescence measurement is repeated (arrow 21). Otherwise, the first characteristic number K1 is determined as the ratio between intensity I2 of the second fluorescence radiation and intensity I1 of the first fluorescence radiation (field 22). Then, the first characteristic number K1 is compared with the first reference value R1 (field 23). If the first characteristic number K1 is smaller than the first reference value R1, bitumen material 2 may be classified as unsuitable for recycling (field 24). If the first characteristic number K1 is larger than the first reference value R1, a comparison is made between the second characteristic number K2 and the second reference value R2 (field 25). If the second characteristic number K2 is smaller than the second reference value R2, bitumen material 2 is considered not to be resistant to ageing (field 26). Only if the second characteristic number K2 is larger than the second reference value R2 is the bitumen material 2 under examination assumed to be ageing-resistant (field 27). Such samples are suitable for reuse. Field 28 indicates the end of the method.

Figure 3:
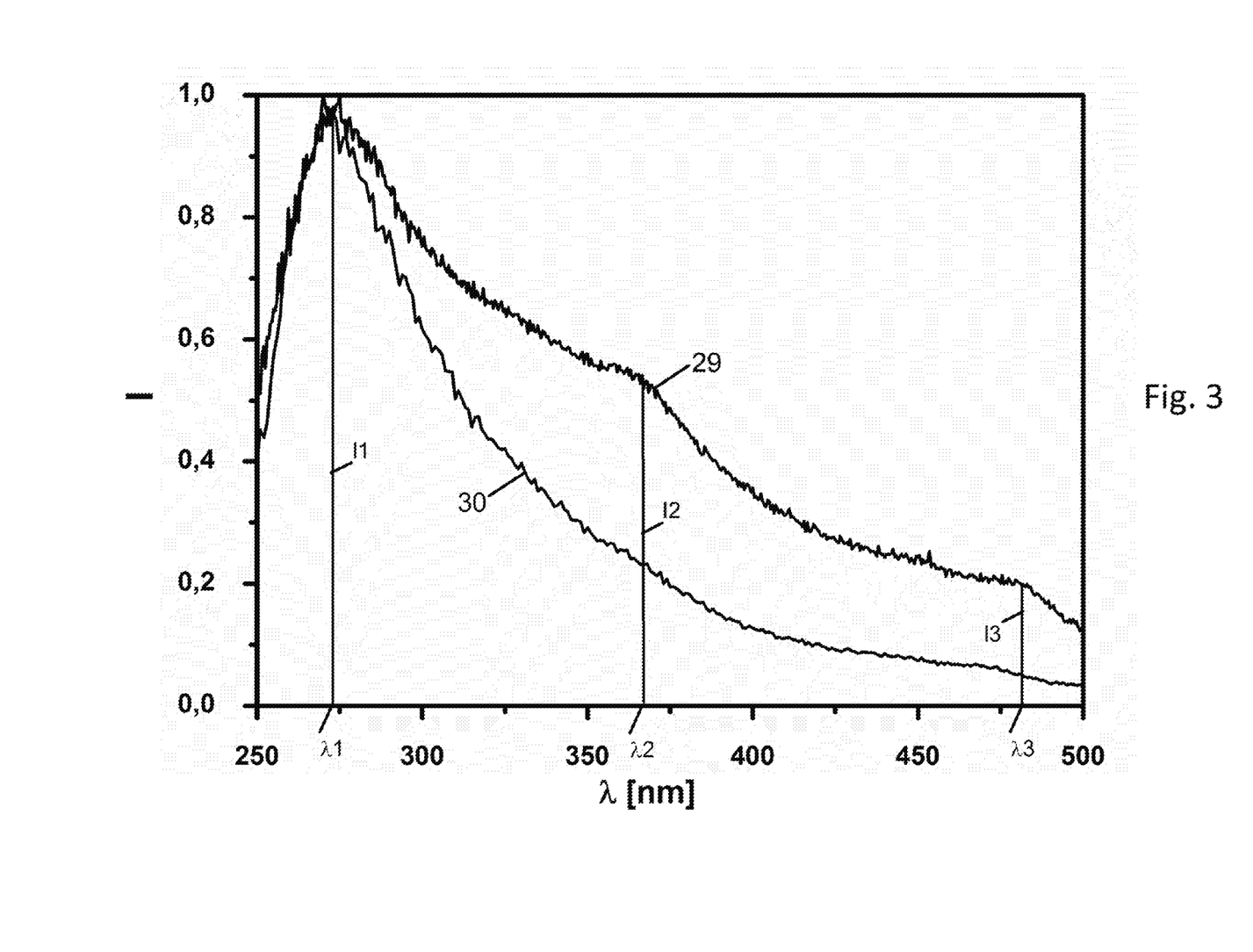
FIG. 3 shows the excitation spectra of one bitumen sample which is resistant to ageing and one bitumen sample which is not resistant to ageing.

FIG. 3 shows a diagram with the excitation spectra 29, 30 of two bitumen samples 2, wherein excitation spectrum 29 refers to a bitumen sample that is resistant to ageing and excitation spectrum 30 refers to a bitumen sample that is not resistant to ageing. Wavelength $\lambda$ of the excitation radiation is plotted on the x-axis, the intensity I of fluorescence on a measurement wavelength of 515 nanometers (nm) is plotted on the y-axis. These show that the fluorescence of the aged bitumen sample, at excitation wavelengths $\lambda$ above the maximum at about 270 nm, is lower than that of the bitumen sample which is resistant to ageing. The spectra also show characteristic local maxima at about 370 nm and 480 nm.

On the basis of these findings, it is preferably provided that the first excitation wavelength $\lambda 1$ of the first excitation radiation 4 is selected from a wavelength range between 260 and 280 nm, in particular substantially 270 nm, the second excitation wavelength $\lambda 2$ of the second excitation radiation 6 is selected from a wavelength range between 350 and 380 nm, in particular substantially 370 nm, and the third excitation wavelength $\lambda 3$ of the third excitation radiation 8 is selected from a wavelength range between 470 and 500 nm, in particular substantially 480 nm. In this way, the first excitation wavelength $\lambda 1$ may be used as a reference for the diminished intensity at larger excitation wavelengths 1. Excitation in the range of the local maxima of the excitation spectrum is particularly advantageous for reasons relating to the measuring procedure.

The principle according to the invention may also be realised with a device (not shown) which is equipped with a radiation unit for applying a substantially monochromatic excitation light having an excitation wavelength of for example 280 nm to the bitumen materials. In this way, the bitumen material is excited to fluorescence. This variant of device 1 is further equipped with a measuring unit which is configured to measure the intensity of a first fluorescence signal excited by the excitation light at a first emission wavelength and the intensity of a second fluorescence signal excited by the excitation light at a second emission wavelength. The device is further equipped with a calculating unit for determining a first characteristic number for the ageing state of the bitumen material from the ratio between the intensity of the second fluorescence signals on the second emission wavelength with the intensity of the first fluorescence signal on the first emission wavelength. The second characteristic number for the ageing state of the bitumen may be formed from the ratio between the intensity of the third fluorescence signal at the third emission wavelength and the intensity of the first fluorescence signal at the first emission wavelength in corresponding manner.

The invention claimed is:

1. A method for determining a material property of a bitumen material, comprising the steps:
    applying a substantially monochromatic first excitation radiation having a first excitation wavelength to the bitumen material;
    measuring an intensity of a first fluorescence radiation excited by the first excitation radiation in a measurement wavelength range;
    applying a substantially monochromatic second excitation radiation having a second excitation wavelength to the bitumen material, wherein the first excitation wavelength and the second excitation wavelength are different;
    measuring an intensity of a second fluorescence radiation excited by the second excitation radiation in the measurement wavelength range; and
    determining a first characteristic number for the material property of the bitumen material from a ratio between the intensity of the second fluorescence radiation and the intensity of the first fluorescence radiations;
    wherein the material property is an ageing state or an ageing resistance of the bitumen material.

2. The method according to claim 1, wherein the first characteristic number is compared with a first reference value for the material property of the bitumen material.

3. The method according to claim 1, further comprising the steps:
applying a substantially monochromatic third excitation radiation having a third excitation wavelength to the bitumen material;
measuring an intensity of a third fluorescence radiation excited by the third excitation radiation in the measurement wavelength range; and
determining a second characteristic number for the material property of the bitumen material from a ratio between the intensity of the third fluorescence radiation and the intensity of the first fluorescence radiation.

4. The method according to claim 3, the second characteristic number is compared with a second reference value.

5. The method according to claim 1, the first excitation wavelength of the first excitation radiation is selected from a wavelength range between 260 and 280 nanometers.

6. The method according to claim 1, wherein the second excitation wavelength of the second excitation radiation is selected from a wavelength range between 350 and 380 nanometers.

7. The method according to claim 3, wherein the third excitation wavelength of the third excitation radiation is selected from a wavelength range between 470 and 500 nanometers.

8. The method according to claim 1, wherein the measurement wavelength range is substantially monochromatic with a measurement wavelength between 390 and 650 nanometers.

9. A device for determining an ageing state or an ageing resistance of a bitumen material, having:
a first radiation device for applying a substantially monochromatic first excitation radiation having a first excitation wavelength to the bitumen material;
a second radiation device for applying a substantially monochromatic second excitation radiation having a second excitation wavelength to the bitumen material, wherein the first excitation wavelength and the second excitation wavelength are different;
a measuring device for measuring an intensity of a first fluorescence radiation excited by the first excitation radiation in a predetermined measurement wavelength range and for measuring an intensity of a second fluorescence radiation excited by the second excitation radiation in the predetermined measurement wavelength range; and
a processing unit with a first ratio forming function for determining a first characteristic number for the ageing state or the ageing resistance of the bitumen material from a ratio between the intensity of the second fluorescence radiation and the intensity of the first fluorescence radiation.

10. The device according to claim 9, further comprising a third radiation device for applying a substantially monochromatic third excitation radiation having a third excitation wavelength to the bitumen material, wherein the measuring device is configured to measure an intensity of a third fluorescence radiation excited by the third excitation radiation in the predetermined measurement wavelength range; and
a second ratio forming function for determining a second characteristic number for the ageing state or the ageing resistance of the bitumen material from a ratio between the intensity of the third fluorescence radiation and the intensity of the first fluorescence radiation.

11. The device according to claim 10, wherein the processing unit has a first database with a first reference value for the ageing state or the ageing resistance of the bitumen material and a first comparison module for comparing the first characteristic number with the first reference value, wherein the processing unit has a second database with a second reference value for the ageing state or the ageing resistance of the bitumen material and a second comparison module for comparing the second characteristic number with the second reference value.

12. The device according to claim 10, wherein the first radiation device has a first light emitting diode for emitting the first excitation radiation having the first excitation wavelength and/or the second radiation device has a second light emitting diode for emitting the second excitation radiation having the second excitation wavelength and/or the third radiation device has a third light emitting diode for emitting the third excitation radiation having the third excitation wavelength.

13. The device according to claim 11, further comprising a display unit for displaying the first characteristic number and/or the second characteristic number and/or the first reference value and/or the second reference value for the ageing state or the ageing resistance of the bitumen material.

14. A method for determining a material property of a bitumen material, comprising the steps:
applying a substantially monochromatic excitation light to the bitumen material;
measuring an intensity of a first fluorescence signal excited by the excitation light at a first emission wavelength;
measuring an intensity of a second fluorescence signal excited by the excitation light at a second emission wavelength; and
determining a first characteristic number for the material property of the bitumen material from a ratio between the intensity of the second fluorescence signal at the second emission wavelength and the intensity of the first fluorescence signal at the first emission wavelength;
wherein the material property is an ageing state or an ageing resistance of the bitumen material.

15. The method according to claim 14, further comprising the steps:
measuring an intensity of a third fluorescence signal excited by the excitation light at a third emission wavelength; and
determining a second characteristic number for the material property of the bitumen material from a ratio between the intensity of the third fluorescence signal at the third emission wavelength and the intensity of the first fluorescence signal at the first emission wavelength.

16. The method according to claim 8, wherein the predetermined measurement wavelength is substantially 525 nanometers.

* * * * *